US010857005B2

(12) United States Patent
Dassonville et al.

(10) Patent No.: US 10,857,005 B2
(45) Date of Patent: Dec. 8, 2020

(54) POSITIONING SYSTEM FOR A BONE RESECTING INSTRUMENTATION AND POSITIONING KIT

(71) Applicant: Tornier, Montbonnot-Saint-Martin (FR)

(72) Inventors: Benjamin Dassonville, Saint Hilaire du Touvet (FR); Jean-Emmanuel Cardon, Domene (FR); Pierric Deransart, Saint Martin d'uriage (FR)

(73) Assignee: Tornier, Montbonnot-Saint-Martin (FR)

( * ) Notice: Subject to any disclaimer, the term of this patent is extended or adjusted under 35 U.S.C. 154(b) by 274 days.

(21) Appl. No.: 15/939,661

(22) Filed: Mar. 29, 2018

(65) Prior Publication Data

US 2018/0280037 A1     Oct. 4, 2018

(30) Foreign Application Priority Data

Mar. 31, 2017  (EP) .................................... 17305391

(51) Int. Cl.
*A61F 2/46* (2006.01)
*A61B 17/16* (2006.01)
*A61B 17/17* (2006.01)

(52) U.S. Cl.
CPC ........ *A61F 2/4657* (2013.01); *A61B 17/1633* (2013.01); *A61B 17/17* (2013.01); *A61B 17/1626* (2013.01); *A61B 17/1659* (2013.01); *A61B 17/1664* (2013.01);
(Continued)

(58) Field of Classification Search
CPC . A61B 17/16; A61B 17/1626; A61B 17/1633; A61B 17/1659; A61B 17/1664; A61B 17/1684; A61B 17/17; A61B 17/1732; A61B 17/1735; A61B 17/1739; A61B 17/1742; A61B 17/1746; A61B 17/1778; A61F 2/4657; A61F 2002/4658; A61F 2002/4662; A61F 2002/4668
See application file for complete search history.

(56) References Cited

U.S. PATENT DOCUMENTS 10,405,928 B2 * 9/2019 Falardeau .............. A61B 34/20
2004/0243148 A1 12/2004 Wasielewski
(Continued)

FOREIGN PATENT DOCUMENTS

WO    WO 2010/030809       3/2010

OTHER PUBLICATIONS

European Search Report issued in EP Application No. 17305391, dated Jun. 28, 2017, in 3 pages.

*Primary Examiner* — Eric S Gibson
(74) *Attorney, Agent, or Firm* — Knobbe, Martens, Olson & Bear, LLP (57) ABSTRACT

This positioning system (100) for a bone resecting instrumentation comprising a resection driver (2), comprises at least one of a gyroscopic sensor (8) integral in motion with the resection driver (2) and adapted to sense a deviation angle (θ) with respect to a reference direction (X), and at least one positioning marker (12; 140) marking a fixed position on the reference direction (X), and a depth sensor (10; 18) integral in motion with the resection driver (2), for detecting a resection depth (d) based on the relative longitudinal positions of the positioning marker (12; 140) and the depth sensor (10).
The invention also concerns a positioning kit including such a positioning system and a separate electronic device.

14 Claims, 4 Drawing Sheets

(52) U.S. Cl.
CPC ... *A61B 17/1684* (2013.01); *A61F 2002/4658* (2013.01); *A61F 2002/4668* (2013.01)

(56) References Cited

U.S. PATENT DOCUMENTS

| | | | | |
|---|---|---|---|---|
| 2010/0312103 A1* | 12/2010 | Gorek | ................. | A61B 6/12 600/425 |
| 2011/0218543 A1* | 9/2011 | van der Walt | ......... | A61B 17/56 606/88 |
| 2013/0053856 A1* | 2/2013 | Penenberg | ......... | A61B 17/3494 606/91 |
| 2013/0307529 A1* | 11/2013 | Baumgartner | ......... | G01D 5/145 324/207.2 |
| 2014/0052149 A1* | 2/2014 | van der Walt | ........ | A61F 2/4657 606/130 |
| 2014/0135773 A1* | 5/2014 | Stein | ................. | G16H 40/67 606/80 |
| 2014/0276871 A1* | 9/2014 | Sherman | ............... | A61F 2/4609 606/91 |
| 2015/0142372 A1* | 5/2015 | Singh | .................. | A61B 5/1071 702/150 |
| 2015/0201918 A1* | 7/2015 | Kumar | ............... | A61B 17/1622 606/104 |
| 2015/0272696 A1* | 10/2015 | Fry | ........................ | A61F 2/4609 606/87 |
| 2016/0022374 A1* | 1/2016 | Haider | ................... | A61B 17/17 606/96 |
| 2016/0038242 A1* | 2/2016 | Lo Iacono | ................ | A61F 2/34 606/86 R |
| 2016/0220315 A1* | 8/2016 | Falardeau | ............. | A61B 34/20 |
| 2016/0242934 A1* | 8/2016 | van der Walt | ..... | A61B 17/1746 |
| 2018/0214283 A1* | 8/2018 | Johannaber | ........... | A61F 2/3859 |
| 2018/0280037 A1* | 10/2018 | Dassonville | ........... | A61B 17/17 |
| 2018/0296365 A1* | 10/2018 | Nielsen | ................. | A61F 2/4607 |
| 2019/0290297 A1* | 9/2019 | Haider | ................... | A61B 34/20 |
| 2019/0357809 A1* | 11/2019 | Borja | .................... | A61B 5/1079 |
| 2020/0054410 A1* | 2/2020 | Pfotenhauer | ........... | A61B 90/03 |

* cited by examiner

POSITIONING SYSTEM FOR A BONE RESECTING INSTRUMENTATION AND POSITIONING KIT

The invention concerns a positioning system for a bone resecting instrumentation. The invention also concerns a positioning kit including such a positioning system and a separate electronic device.

The joint replacement surgery, for example for shoulder or hip, requests preparation steps during which the articular surfaces of the joints are resected to receive the articular implants. To this end, ancillary tools, such as reamers, are used to cut the bone. During this resection operation, the surgeon needs to control that the direction and depth of the resection respects the planned operation, and that the reamer or the resection tool does not deviate from its direction or goes too deep into the bone. A reference pin inserted in the bone is generally used to mark the reference direction along which the cutting should be made. However, when the surgeon pushes the reamer forward, the configuration of the surrounding tissues may lead to pushing along a deviated direction, provoking bending the reference pin and losing the correct resection direction.

US 2015/0374387 discloses a mechanical alignment sensing technique that does not provide a satisfactory accuracy. This reference does no deal with detection of the reaming depth.

U.S. Pat. No. 8,617,170 discloses a patient-specific surgical instrumentation assembly including customized blocks equipped with sensors and calculator that perform numerous calculations to determine the position of a spindle relative to the bone. This technique involves significant programming and is costly due to the customized instruments and heavy memory for calculations.

The aim of the invention is to provide a new positioning system, which allows a surgeon to quickly, simply and with accuracy control the direction and/or depth of a resection operation.

To this end, the invention concerns a positioning system for a bone resecting instrumentation comprising a resection driver, wherein the positioning system comprises at least one of:
- a gyroscopic sensor integral in motion with the resection driver and adapted to sense a deviation angle with respect to a reference direction,
- at least one positioning marker marking a fixed position on the reference direction, and a depth sensor integral in motion with the resection driver, for detecting a resection depth based on the relative longitudinal positions of the positioning marker and the depth sensor.

Thanks to the invention, the surgeon is provided with quickly obtainable information on the accuracy of the depth and/or orientation of the cut he is performing, allowing better positioning of the surgical implant.

According to further aspects of the invention which are advantageous but not compulsory, such a positioning system may incorporate one or several of the following features:

The positioning system comprises means to emit information signals depending on the angular deviation of the resection driver with respect to the reference direction and/or on the resection depth.

The positioning system comprises a sound emitter adapted to emit sounds depending on the angular deviation of the resection driver with respect to the reference direction and/or on the resection depth.

The positioning system comprises visual signal emitters for emitting signals depending on the angular deviation of the resection driver with respect to the reference direction and/or on the resection depth.

The positioning system comprises means for sending depth and/or deviation information to a separate electronic device.

The positioning system comprises a reference pin intended to be inserted in a fixed orientation in a bone for marking the reference direction.

The at least one positioning marker is provided on the reference pin.

The at least one positioning marker is formed by a plurality of transversal positioning grooves provided on an outer surface of the reference pin, and the depth sensor comprises an optical signal emitter on a first side of the reference pin, a receiver adapted to detect the optical signal on the other side of the reference pin, and counting means for determining the resection depth on the basis of the number of transversal positioning grooves that the resection driver passes by.

The at least one positioning marker is formed by a magnetic element provided at a fixed location along the reference pin, and the depth sensor comprises a magnetic sensor adapted to detect magnetic field variations induced by the longitudinal displacement of the resection driver with respect to the magnetic element, and a counting means for determining the resection depth on the basis of the magnetic field variations.

The magnetic sensor is a Hall-effect sensor.

The gyroscopic sensor and/or the depth sensor are provided in a housing attached removably to the resection driver.

The positioning system comprises means to set a reference point before resecting, this reference point being used to mark the reference direction.

The invention also concerns a positioning kit including:
- a positioning system for a bone resecting instrumentation comprising a resection driver, the positioning system comprising at least one of:
  - a gyroscopic sensor integral in motion with the resection driver and adapted to sense a deviation angle with respect to a reference direction,
  - at least one positioning marker marking a fixed position on the reference direction, and a depth sensor integral in motion with the resection driver, for detecting a resection depth based on the relative longitudinal positions of the positioning marker and the depth sensor,
- a separate electronic device,
the positioning system comprising means for sending depth and/or deviation information to the separate electronic device.

The invention will now be explained in correspondence with the annexed figures, as an illustrative example. In the annexed figures.

Figure 1:
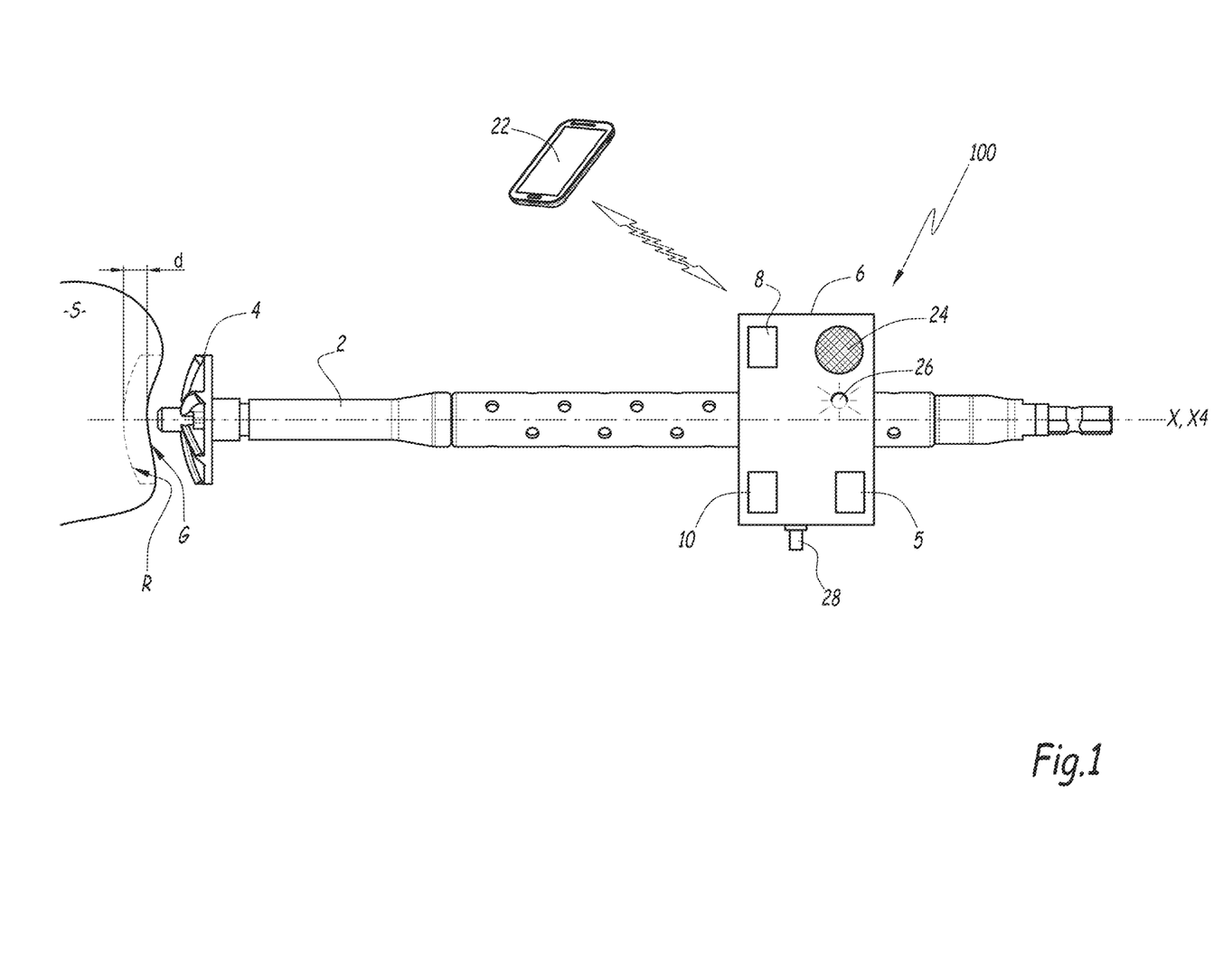
FIG. 1 is a side view of a positioning system according to the invention, a resection driver, and a reamer positioned against a scapula.

FIG. 1 shows a positioning system 100 for a bone resecting instrumentation. The bone resecting instrumentation comprises a resection driver 2, which is formed by an elongated part on which is mounted a cutting member. In the drawn example, the cutting member is a reamer 4 that is a circular shaped part whose purpose is to cut the bone by a rotative movement. The resection driver 2 and the reamer 4 share a central longitudinal axis X4.

According to other embodiments, the cutting member can also be of another type, such as a drill, a compactor, a tap, for example.

On FIG. 1 is also shown a scapula S of a shoulder of a patient whose shoulder joint needs to be totally or partially replaced. The scapula S comprises a glenoid surface G, which is intended to be resected by the reamer 4 in order to make room for a glenoid replacement implant, not shown.

According to a non-shown alternative embodiment, the invention can also be applied to other joint replacement surgical operations, such as on the hand, wrist or foot.

To correctly position the implant, the cavity made by the reamer 4 has to be accurately resected, and a reference resection direction X is therefore determined during pre-operational planning using imaging, for example CT scans, MRI, X-rays or the like. The positioning system 100 includes a reference pin 14 inserted in the scapula S to mark the reference direction X.

Along the reference direction X, two parameters are significant to guarantee a correct positioning of the shoulder implant. The first parameter is the accuracy of the surgeon in respecting the angle defined by the reference direction X with respect to the bone while performing the resection; the second is the depth d of the resection, represented in ghost lines by a bottom surface R, with respect to the initial glenoid surface G.

Figure 2:
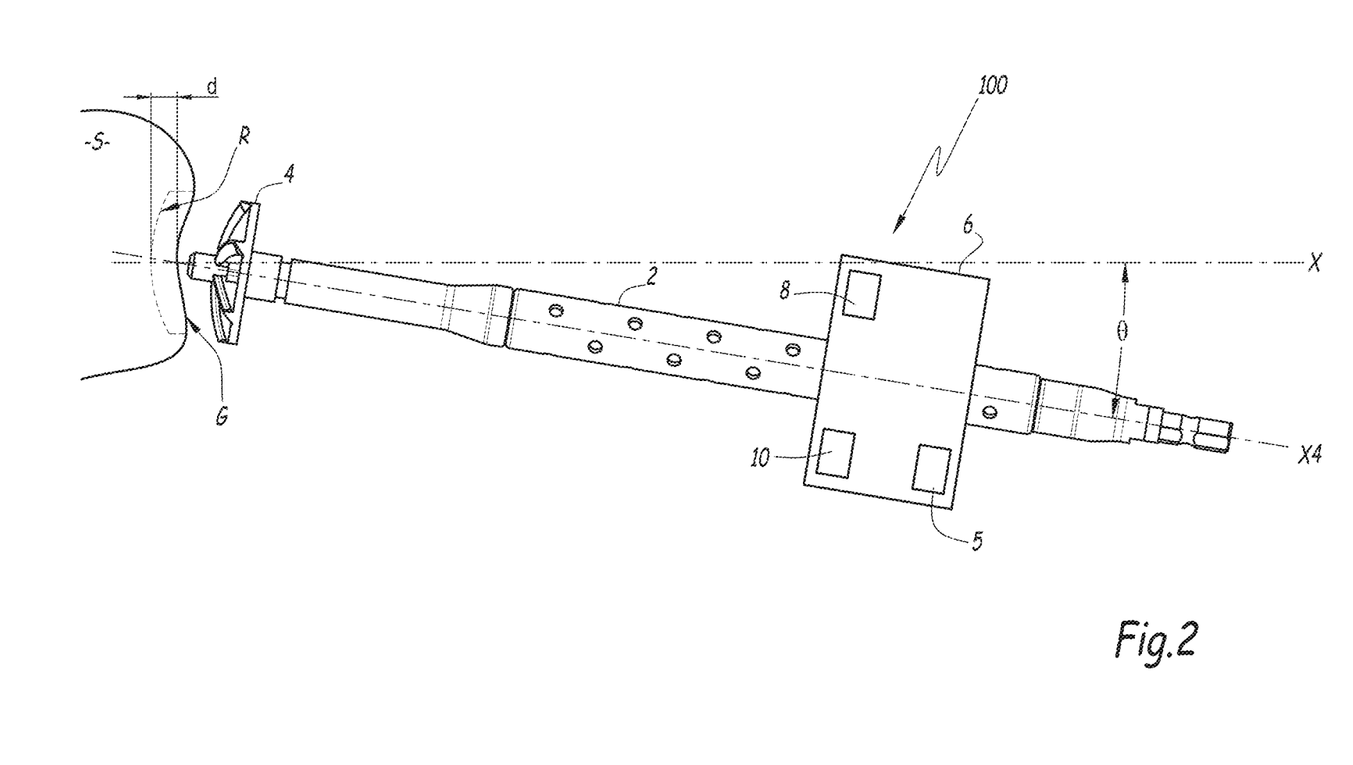
FIG. 2 is a view similar to FIG. 1, with the resection driver being deviated from a reference direction.

To control the deviation angle θ of the central axis X4 of the resection driver 2 with respect to the reference direction X, the positioning system 100 may comprise a gyroscopic sensor 8 that is integral in motion with the resection driver 2. The gyroscopic sensor 8 is adapted to sense the deviation angle θ with respect to the reference direction X.

For example, the gyroscopic sensor 8 is able to deliver rotation angles around three Cartesian axes of the space, one being aligned with the central longitudinal axis X4. During a translational reaming motion, the gyroscopic sensor 8 will detect rotation around axis X4, and around axes perpendicular to axis X4. These latter rotations will give the displacement of the gyroscopic sensor 8 with respect to its previous position. The deviation angle θ can then be calculated. Rotations around axis X4 are neglected as they are not representative of deviation.

The positioning system 100 may comprise means to set a reference point before resecting, this reference point being used to mark the reference direction X. Such means may include, for example a push button 28 on the housing 6. This reference point can be set with the resection driver 2 mounted on the reference pin 14 and positioned just above the glenoid surface G. This reference point and used by the gyroscopic sensor 8 as a starting point to detect the angular deviation θ.

The positioning system 100 comprises a sound emitter 24 adapted to emit sounds depending on the angular deviation θ of the resection driver 2 with respect to the reference direction X. For example, the frequency of the sounds can vary depending on the value of the angular deviation θ.

The positioning system 100 may also comprise visual signal emitters 26 (for emitting signals depending on the angular deviation θ. For example, the color of the signals can be chosen depending on the value of the angular deviation θ, for example a green light for a deviation comprised within an acceptable range, an orange color for a deviation exceeding the acceptable range and being in a first exceeding range, and a red color for deviation values exceeding the first exceeding range corresponding to the orange signal.

The sensing of the deviation θ may consist in determining the actual position of the gyroscopic sensor 8, with respect to two cones, defined by their central axis corresponding to the reference axis X, and with their apex angle. A first cone may define the acceptable range of deviation, which may for example be of a minimal 3 degrees, and for which there is no sound emission. The second cone may define average deviation, for example between 3 and 5 degrees, and for which an orange light and a discontinuous sound are emitted. If the position of the gyroscopic sensor 8 is detected outside of this second cone, red light and continuous sound may be emitted.

In addition to the gyroscopic sensor 8, the positioning system 100 comprises at least one positioning marker marking a fixed position on the reference direction X, and a depth sensor 10 integral in motion with the resection driver 2, for detecting the resection depth d based on the relative longitudinal positions of the positioning marker and the depth sensor 10. The positioning system 100 may therefore comprise either the deviation sensor, either the depth sensor, or both.

The at least one positioning marker is provided on the reference pin 14. In a first embodiment represented on FIG. 3, the at least one positioning marker is formed by a magnetic element 12 provided at a fixed location along the reference pin 14. The resection driver 2 comprises an inner bore 20 in which the reference pin 14 is inserted. The resection driver 2 is able to slide with respect to the reference pin 14 along axis X to progressively ream the scapula S.

Figure 3:
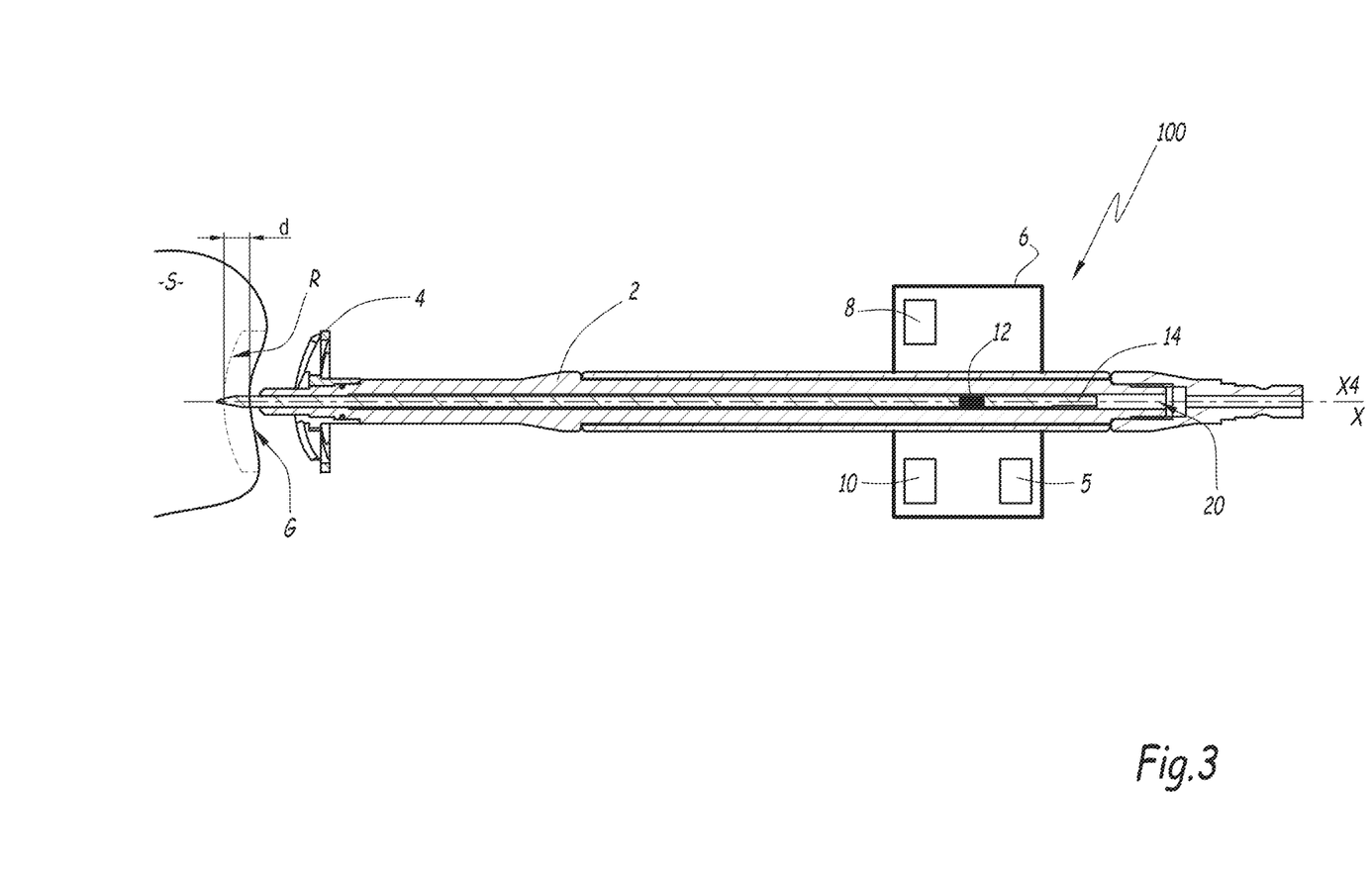
FIG. 3 is a sectional view of the elements of FIG. 1, the resection driver being mounted along a reference pin belonging to the positioning system of FIG. 1.

The depth sensor 10 is formed by a magnetic sensor adapted to detect magnetic field variations induced by the longitudinal displacement of the magnetic sensor 10 attached to the resection driver 2, with respect to the magnetic element 12. The positioning system 100 also includes counting means for determining the resection depth d on the basis of the magnetic field variations.

For example, the magnetic sensor 10 can be a Hall-effect sensor.

Figure 4:
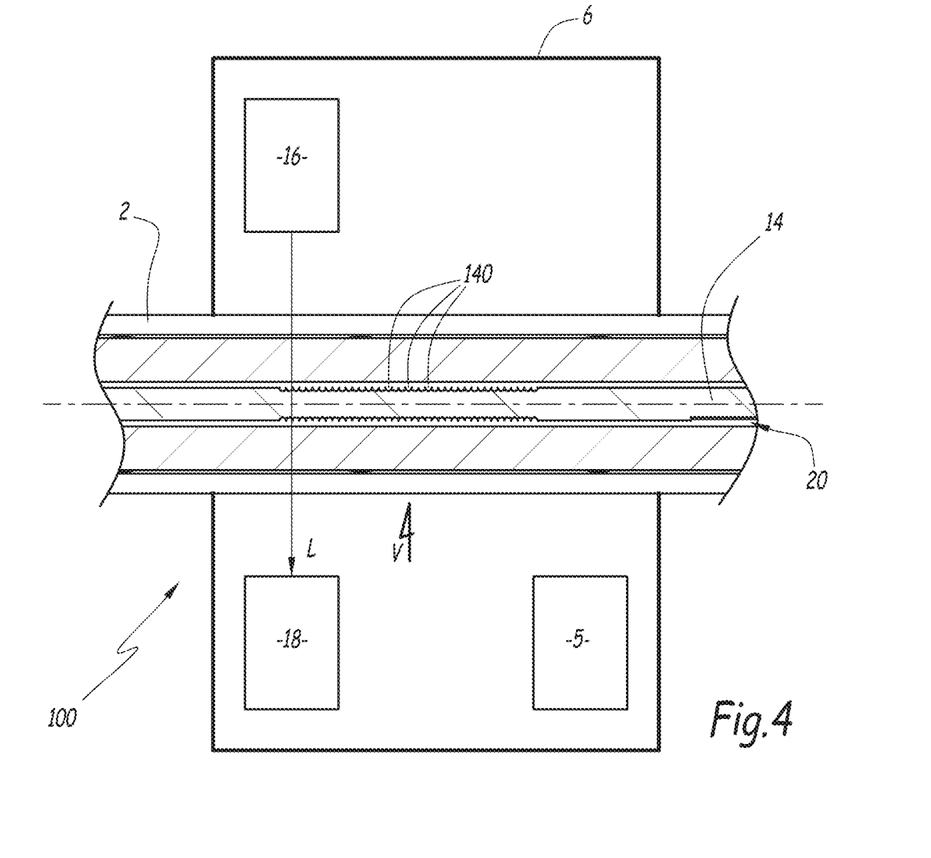
FIG. 4 is a view of a portion of a positioning system according to a second embodiment of the invention.
Figure 5:
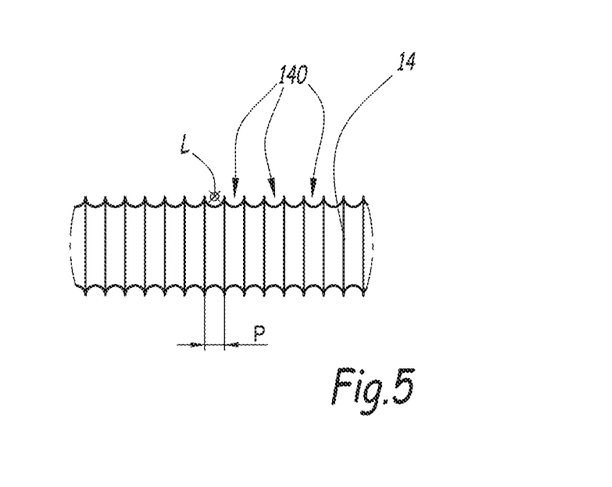
FIG. 5 is a view along arrow V on FIG. 4, of a reference pin of the positioning system of FIG. 4.

According to a second embodiment represented on FIGS. 4 and 5, the at least one positioning marker is provided in the form of a plurality of transversal positioning grooves 140 provided on an outer surface of the reference pin 14. These grooves 140 may have, as shown in the drawn example, a round shape, and any other appropriate shapes such as a V-shape, a square shape, etc., that form ridges or have specific predetermined distances or lengths between them.

In such a case, the depth sensor comprises a laser signal emitter 16 on a first side of the reference pin 14, and a laser receiver 18 adapted to detect a laser signal L on the other side of the reference pin 14. The laser signal L is oriented tangentially to the surface of the reference pin 14 so that the ridges or specific predetermined distances or lengths separating the grooves 140 provoke interruptions of the laser signal L. These laser signal interruptions can be detected by counting means that are provided in the positioning system 100 and that determine the resection depth d on the basis of the number of transversal positioning grooves 140 that the resection driver 2 passes by during resection. The number of transversal positioning grooves 140 passed by is given by the number of interruptions of the laser signal L. By distributing the grooves 140 according to a determined pitch P, the resection depth d can be calculated.

The position system 100 may comprise sound signals emitters 24 or visual signals emitters 26 emitting information signals depending on the resection depth d similar to the ones described for the angular deviation.

More generally, the position system 100 comprises information signal emission means for emitting signals representative of the deviation and/or depth of any type, such as visual, audio, vibrations, and the like.

As shown on the figures, the gyroscopic sensor 8 and/or the depth sensor 10 may be provided in a housing 6 attached removably to the resection driver 2. For example, the housing 6 may comprise elastic means adapted to retain the housing 6 on the resection driver 2, and to easily remove the housing 6 to attach it to another resection driver for another resecting operation.

The positioning system 100 may comprise means for sending depth and/or deviation information to a separate electronic device 22, such as a smartphone, a laptop, smart glasses, tablet computer, touchscreen tablet, mobiles devices or phones or computers, or any display mean that can be worn by a surgeon or any medical personnel, or to another display mean present in an operation room.

The positioning system 100 may form a positioning kit with the separate electronic device, such as a smartphone, a laptop, smart glasses, tablet computer, touchscreen tablet, mobiles devices or phones or computers, or any display mean as mentioned here-above, the positioning system comprising means for sending depth and/or deviation information to the separate electronic device 22.

According to a non-shown embodiment, the laser signal L can be replaced by any other optical signal adapted to fulfill the sensing function, for example other light signals having determined wave lengths. In such a case, the laser emitter 16 may be more generally a light emitter, and the laser sensor 18 may be more generally an optical sensor.

The data delivered by the gyroscopic sensor 8 and the depth sensor 10 or 18 may be received and processed by an electronic processing unit 5, integrated in the housing 6. The electronic central unit 5 may provide calculation means to determine the angular deviation θ on the basis of the data of the gyroscopic sensor 8, and the resection depth d on the basis of the data of the magnetic sensor 10 or the optical sensor 18. The electronic central unit 5 may also control the sound or light emitting means of the positioning system 100.

The means for sending depth and/or deviation information to a separate electronic device may be comprised in the electronic processing unit 5, and may be formed by any signal emitter adapted to send signals to the various previously mentioned electronic devices.

According to a non-shown embodiment, the above-mentioned processing, calculations and controlling functions may be provided by distinct electronic central units.

According to a non-shown embodiment, the positioning system 100 may comprise only the positioning marker and the depth sensor, and comprise no gyroscopic sensor.

The invention claimed is:

1. A positioning system for a bone resecting instrumentation comprising a resection driver, at least one positioning marker for marking a fixed position on a reference direction, a depth sensor integral in motion with the resection driver for detecting a resection depth based on a relative longitudinal position of the positioning marker with respect to the depth sensor, and a reference pin configured to be inserted in a fixed orientation in a bone for marking the reference direction, wherein the at least one positioning marker is provided on the reference pin.

2. The positioning system according to claim 1, wherein the positioning system comprises a gyroscopic sensor integral in motion with the resection driver and adapted to sense a deviation angle with respect to the reference direction.

3. The positioning system according to claim 2, wherein the gyroscopic sensor is provided in a housing attached removably to the resection driver.

4. The positioning system according to claim 1, wherein the positioning system comprises means to emit information signals depending on an angular deviation of the resection driver with respect to the reference direction, sensed by a gyroscopic sensor integral in motion with the resection driver, and/or on the resection depth.

5. The positioning system according to claim 4, wherein the positioning system comprises a sound emitter adapted to emit sounds depending on the angular deviation of the resection driver with respect to the reference direction and/or on the resection depth.

6. The positioning system according to claim 4, wherein the positioning system comprises visual signal emitters for emitting signals depending on the angular deviation of the resection driver with respect to the reference direction and/or on the resection depth.

7. The postioning system according to claim 1, wherein the positioning system comprises means for sending the resection depth and/or a deviation angle with respect to the reference direction sensed by a gyroscopic sensor integral in motion with the resection driver, to a separate electronic device.

8. The positioning system according to claim 1, wherein the at least one positioning marker is formed by a plurality of transversal positioning grooves provided on an outer surface of the reference pin, and the depth sensor comprises an optical signal emitter on a first side of the reference pin, a receiver adapted to detect the optical signal on a second side of the reference pin, and counting means for determining the resection depth based on a number of transversal positioning grooves that the resection driver passes by.

9. The positioning system according to claim 1, wherein the at least one positioning marker is formed by a magnetic element provided at a fixed location along the reference pin, and the depth sensor comprises a magnetic sensor adapted to detect magnetic field variations induced by the longitudinal displacement of the resection driver with respect to the magnetic element, and a counting means for determining the resection depth on the basis of the magnetic field variations.

10. The positioning system according to claim 9, wherein the magnetic sensor is a Hall-effect sensor.

11. The positioning system according to claim 1, wherein the depth sensor is provided in a housing attached removably to the resection driver.

12. The positioning system according to claim 1, wherein the positioning system comprises means to set a reference point before resecting, the reference point being used to mark the reference direction.

13. A positioning kit including:
a positioning system for a bone resecting instrumentation comprising a resection driver, at least one positioning marker for marking a fixed position on a reference direction, and a depth sensor integral in motion with the resection driver for detecting a resection depth based on a relative longitudinal position of the positioning marker with respect to the depth sensor, and
a separate electronic device, the positioning system comprising means for sending depth information to the separate electronic device.

14. The positioning kit according to claim 13, wherein the positioning system comprises a gyroscopic sensor integral in motion with the resection driver and adapted to sense a deviation angle with respect to the reference direction, and wherein the positioning system comprises means for sending deviation information to the separate electronic device.

\* \* \* \* \*

UNITED STATES PATENT AND TRADEMARK OFFICE
CERTIFICATE OF CORRECTION

PATENT NO. : 10,857,005 B2  
APPLICATION NO. : 15/939661  
DATED : December 8, 2020  
INVENTOR(S) : Benjamin Dassonville Page 1 of 1

It is certified that error appears in the above-identified patent and that said Letters Patent is hereby corrected as shown below:

In the Specification

In Column 3, Line 66, delete "(for" and insert --for--.

In the Claims

In Column 6, Line 27, Claim 7, delete "postioning" and insert --positioning--.

Signed and Sealed this  
Twenty-third Day of February, 2021

Drew Hirshfeld  
*Performing the Functions and Duties of the*  
*Under Secretary of Commerce for Intellectual Property and*  
*Director of the United States Patent and Trademark Office*